(12) United States Patent  
Murry et al.

(10) Patent No.: US 6,570,020 B2
(45) Date of Patent: May 27, 2003

(54) PROCESS FOR THE PREPARATION OF NON-STEROIDAL GLUCOCORTICOID RECEPTOR MODULATORS

(75) Inventors: Jerry A. Murry, New York, NY (US); Timothy D. White, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/008,619

(22) Filed: Oct. 22, 2001

(65) Prior Publication Data

US 2002/0087005 A1 Jul. 4, 2002

Related U.S. Application Data

(60) Provisional application No. 60/243,873, filed on Oct. 27, 2000.

(51) Int. Cl.$^7$ ............................................. C07D 213/40
(52) U.S. Cl. ....................................................... 546/337
(58) Field of Search ................................. 546/337, 336

(56) References Cited

U.S. PATENT DOCUMENTS 6,380,223 B1 * 4/2002 Dow et al. ............... 514/238.2

OTHER PUBLICATIONS d'Angelo, J., et al., *The Asymmetric Michael Addition Reactions Using Chiral Imines; Tetrahedro: Asymmetry*, vol. 3, No. 4, p. 459–505; (1992).
Drakesmith, F. G., et al., *The Preparation and Reactions of Lithium Derivatives of Trifluoropropene and Trifluoropropyne; Journal of Organic Chemistry*; vol. 33, p. 280–285; (1968).
A. L. Henne, et al., *Trifluoropropyne. II. The Triple Bond and the Acetylenic Hydrogen, Journal of the American Chemical Society*, vol. 74, p. 650–652. (1952).
Corey, E. J., et al., *Total Synthesis of Longifolene; Journal of the American Chemical Society*, vol. 86, p. 478–485; (1964).
Tschaen, D. M., et al., *An Improved Procedure for Aromatic Cyanation, Synthetic Communications*; vol. 24, p. 887–890; (1994).
Deraedt, R., et al., *17α–alkynyl–11β, 17–dihydroxyandrostane Derivatives: A new Class of Potent Glucocoritcoids, Steroids*; vol. 38, No. 6, p. 651–666. (1981).
Purdy, R. H., et al., *Radioimmunoassay of 3α–hydroxy–5α–pregnan–20–one in Rat and Human Plasma, Steroids*; vol. 55, p. 290–296; (1990).
Piers, E., et al., *Total Synthesis of the Diterpenoids (±)–Verrucosan–2β–ol, (−±)–Homoverrucosan–5β–ol. An Approach to the Synthesis of the Sesterterpenoid Variecolin, Tetrahedron Letters*; vol. 38, No. 51, p. 8815–8818; (1997).
Hosoda, H., et al., *Chemical Conversion of Corticosteroids to 3α,5β–Tetrahydro Derivatives. Synthesis of Allotetrahydro–11–deoxycortisol Glucuronides; Chem. Pharm. Bull.*, 33(10) p. 4281–4287, (1985).

* cited by examiner

Primary Examiner—Zinna Northington Davis
(74) Attorney, Agent, or Firm—Peter C. Richardson; Gregg C. Benson; B. Timothy Creagan

(57) ABSTRACT

A process for preparing a compound of the formula

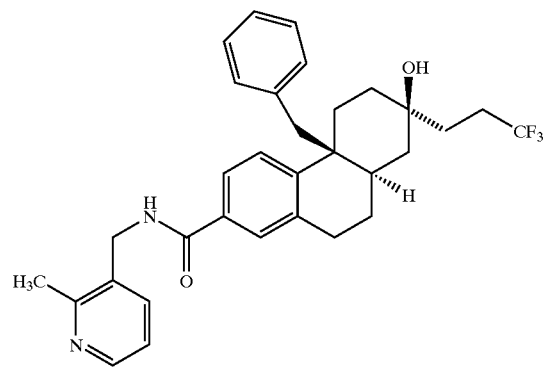

I useful as a non-steroidal glucocorticoid receptor modulator.

10 Claims, No Drawings

PROCESS FOR THE PREPARATION OF NON-STEROIDAL GLUCOCORTICOID RECEPTOR MODULATORS

CROSS REFERENCE TO RELATED APPLICATION

This non-provisional application is based upon and claims priority from U.S. provisional application No. 60/243,873, filed Oct. 27, 2000.

BACKGROUND OF THE INVENTION

The present invention relates to a process for the preparation of non-steroidal glucocorticoid receptor modulators.

Nuclear receptors are classically defined as a family of ligand dependent transcription factors, that are activated in response to ligand binding (R. M. Evans, 240 Science, 889 (1988)). Members of this family include the following receptors: glucocorticoid, mineralocorticoid, androgen, progesterone and estrogen. Naturally occurring ligands to these receptors are low molecular weight molecules that play an important role in health and in many diseases. Excesses or deficiencies of these ligands can have profound physiological consequences. As an example, glucocorticoid excess results in Cushing's Syndrome, while glucocorticoid insufficiency results in Addison's Disease.

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for some of the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist.

SUMMARY OF THE INVENTION

The present invention relates to a process for preparing a compound of the formula

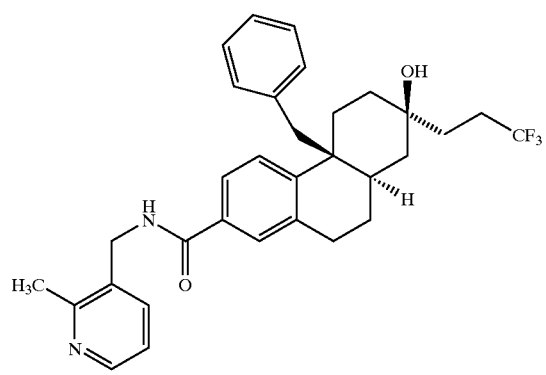

I comprising reacting a compound of the formula

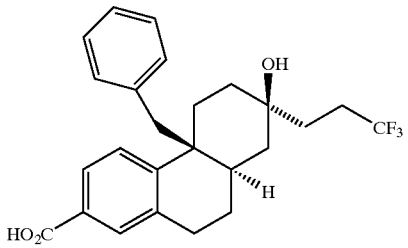

II with an amide of the formula

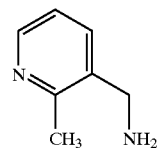

in the presence of 1,1'-carbonyldiimazole.

The present invention further relates to a process for preparing a compound of the formula

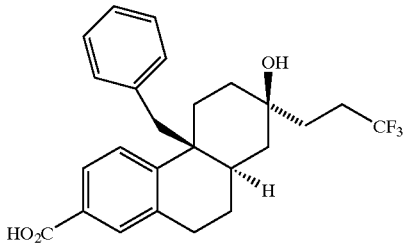

II comprising reacting a compound of the formula

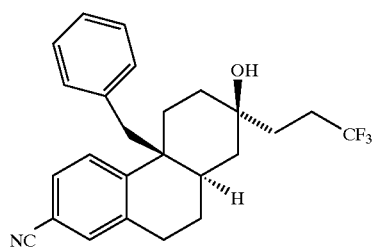

III with aqueous sodium hydroxide in a polar protic solvent.

The present invention further relates to a process for preparing a compound of the formula

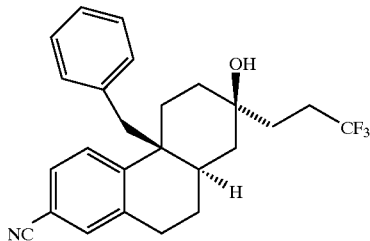

III comprising reducing a compound of the formula

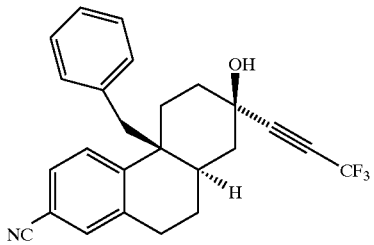

IV with hydrogen in the presence of a catalyst.

The present invention further relates to a process for preparing a compound of the formula

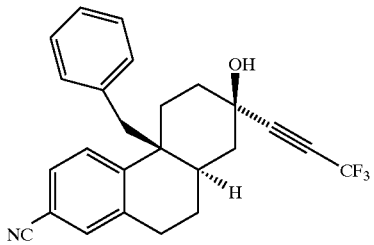

IV comprising reacting the compound of the formula

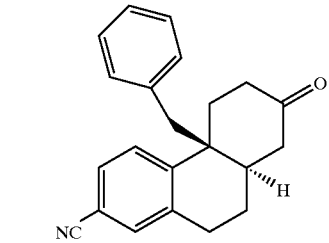

V with trifluoromethylpropyne.

The present invention further relates to a process for preparing a compound of the formula

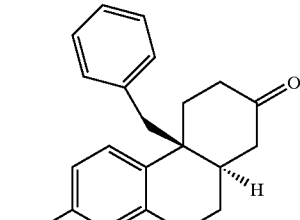

V comprising reducing a compound of the formula

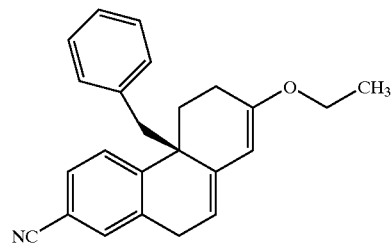

VI with hydrogen in the presence of a catalyst and potassium carbonate.

The present invention further relates to a process for preparing a compound of the formula

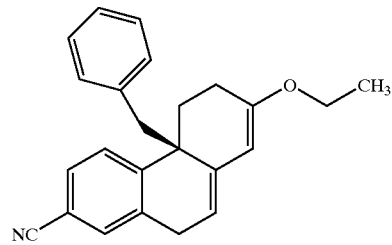

VI comprising reacting a compound of the formula

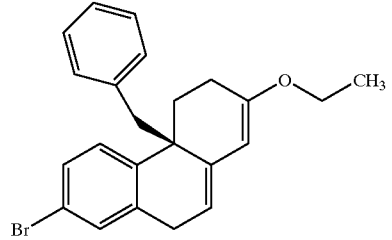

VII with a cyanide source in the presence of a catalyst.

The present invention further relates to a process for preparing a compound of the formula

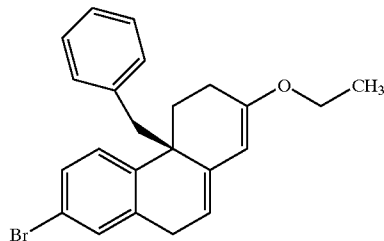
VII comprising reacting a compound of the formula

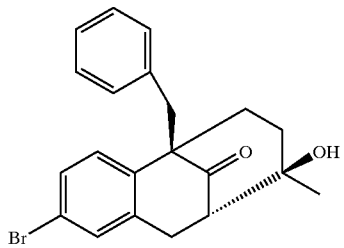
VIII with sodium methoxy.

The present invention further relates to a process for preparing a compound of the formula

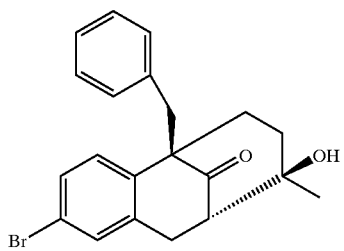
VIII comprising reacting a compound of the formula

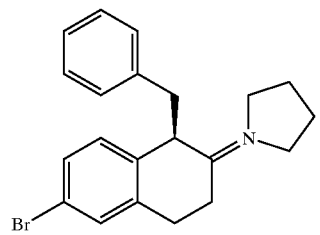
IX with methyl vinyl ketone.

The present invention further relates to a process for preparing a compound of the formula

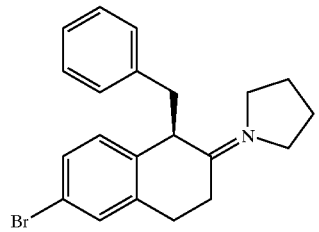
IX comprising reacting a compound of the formula

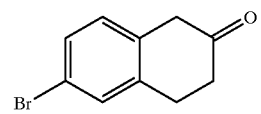
X with pyrrolidine followed by reacting the resultant pyrrolidine enamine intermediate with a benzyl halide.

The present invention relates to a process for preparing a compound of the formula

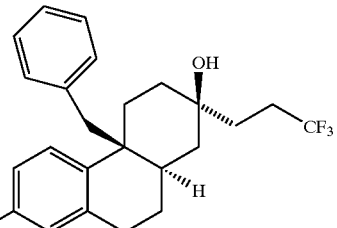
I comprising (a) reacting a compound of the formula

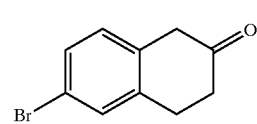
X with pyrrolidine followed by reacting the resultant pyrrolidine enamine intermediate with a benzyl halide to form the compound of formula IX

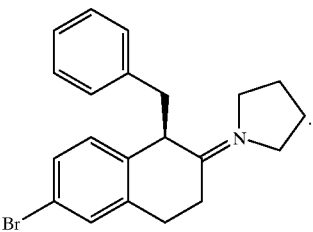
IX (b) reacting the compound of formula IX so formed with methyl vinyl ketone to form the compound of formula VIII

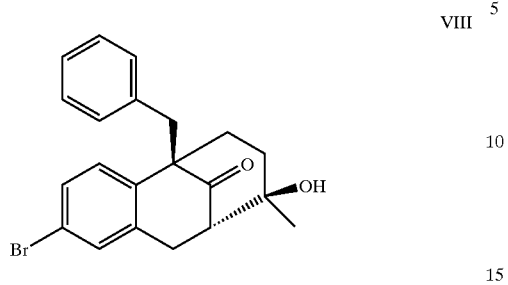

VIII (c) reacting the compound of formula VIII so formed with sodium methoxy to form the compound of formula VII

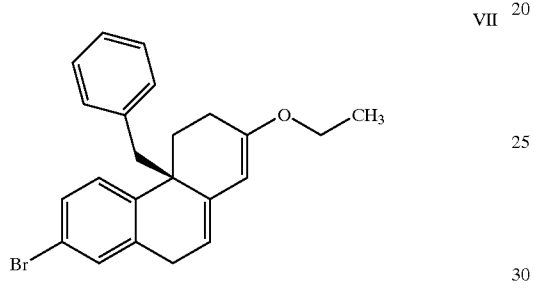

VII (d) reacting the compound of formula VII so formed with a cyanide source in the presence of a catalyst to form the compound of formula VI

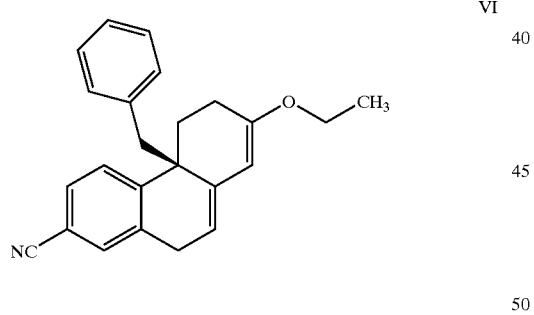

VI (e) reducing the compound of formula VI so formed with hydrogen in the presence of a catalyst and potassium carbonate to form the compound of formula V

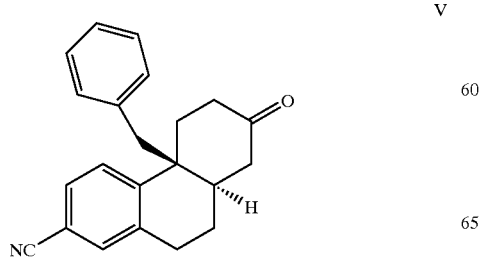

V (f) reacting the compound of formula V so formed with trifluoromethylpropyne to form the compound of formula IV

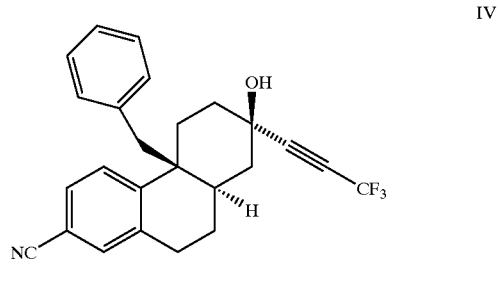

IV (g) reducing the compound of formula IV so formed with hydrogen in the presence of a catalyst to form the compound of formula III

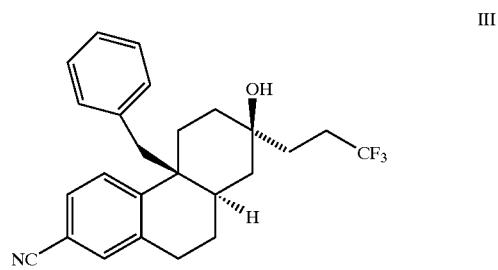

III (h) reacting the compound of formula III so formed with aqueous sodium hydroxide in a polar protic solvent to form the compound of formula II

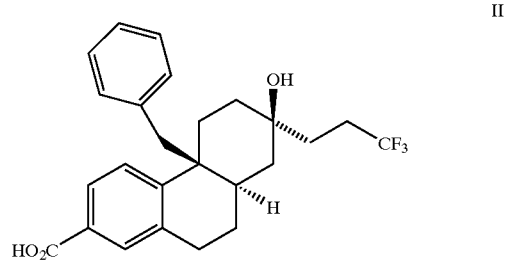

II (i) reacting the compound of formula II so formed with an amide of the formula

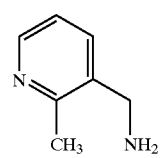

in the presence of 1,1'-carbonyldiimazole.

The present invention relates to a process for preparing a compound of the formula

VIII

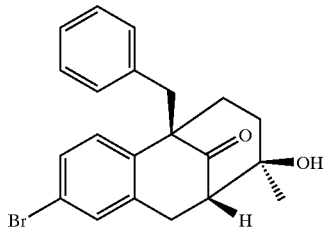

comprising reacting the compound of the formula

XXII

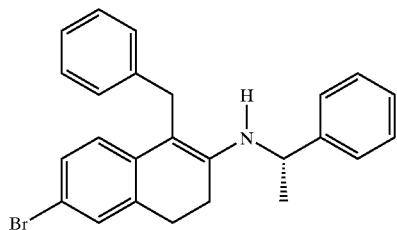

with methyl vinyl ketone.

The present invention further relates to a process for preparing a compound of the formula

XXII

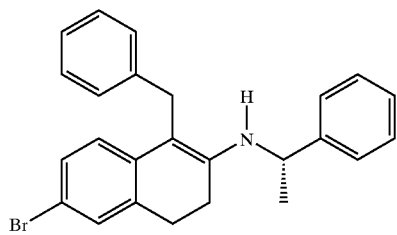

comprising reacting a compound of the formula

XXIII

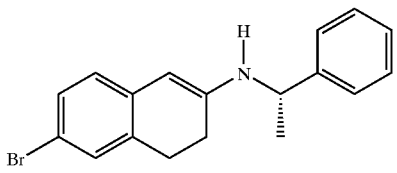

with a benzyl halide.

The present invention further relates to a process for preparing a compound of the formula

XXIII

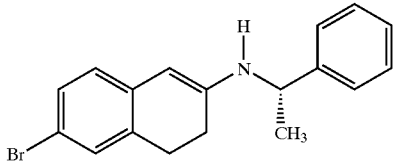

comprising reacting the compound of the formula

X

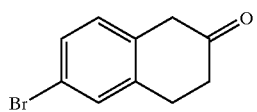

with an amine of the formula

XXIV

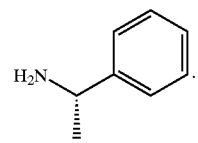

The present invention relates to a process for preparing a compound of the formula

XX

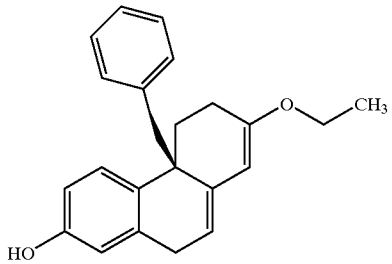

comprising reacting the compound of the formula

VII

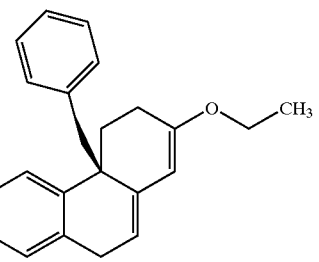

with a borane or a borate.

The present invention relates to a process for preparing a compound of the formula

XVII comprising reacting a compound of the formula

XVIII

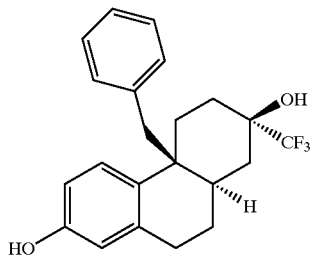

with a compound of the formula

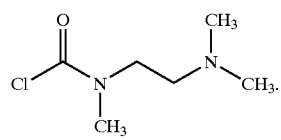

The present invention further relates to a process for preparing a compound of the formula

XVIII

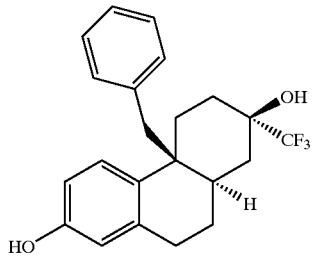

comprising reacting the compound of the formula

XIX

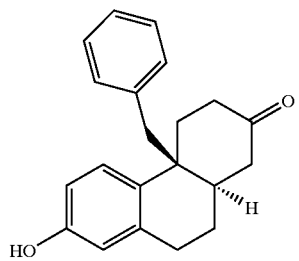

with trimethylsilyl trifluoromethane.

The present invention relates to a process for preparing a compound of the formula

XXVII

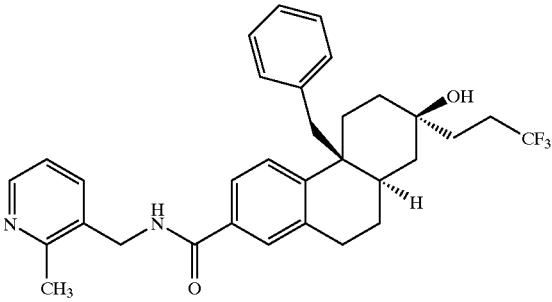

comprising reacting a compound of the formula

XI

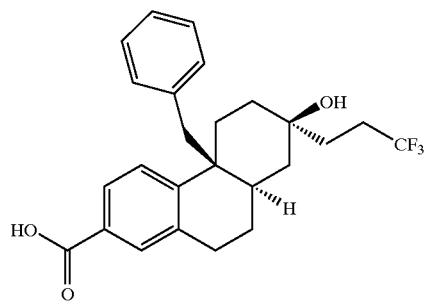

with an amine of the formula

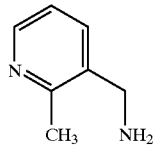

in the presence of 1,1'carbonydiimidazole.

The present invention further relates to a process for preparing a compound of the formula

XI

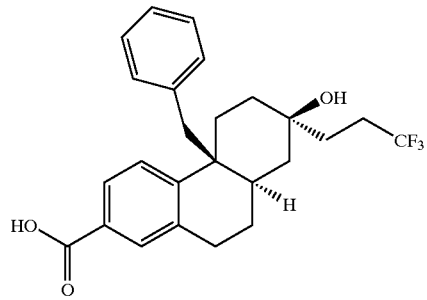

comprising reacting the compound of the formula

XII

[structure]

with aqueous sodium hydroxide in a polar protic solvent.

The present invention further relates to a process for preparing a compound of the formula

XII

[structure]

comprising reducing the compound of formula XIII

XIII

[structure]

with hydrogen in the presence of a catalyst.

The present invention further relates to a process for preparing a compound of the formula

XIII

[structure]

is formed comprising reacting the compound of the formula

XIV

[structure]

with trifluoromethylpropyne.

The present invention further relates to a process for preparing a compound of the formula

XIV

[structure]

is formed comprising reducing the compound of formula XV

XV

[structure]

with hydrogen in the presence of a catalyst.

The present invention further relates to a process for preparing a compound of the formula

XV

[structure]

comprising reacting the compound of the formula

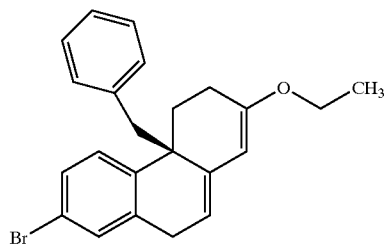

VII with a cyanide source.

The present invention relates to a compound of the formula

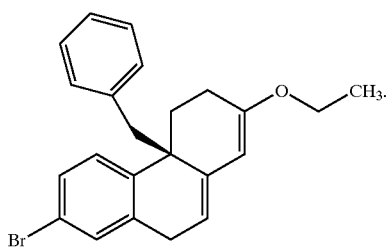

VII

The present invention relates to a compound of the formula

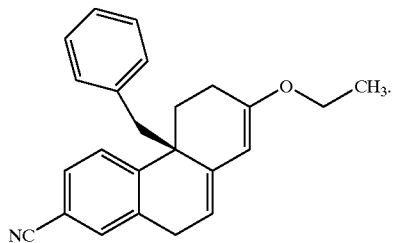

VI

The present invention relates to a compound of the formula

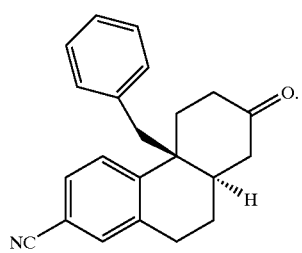

V

The present invention relates to a compound of the formula

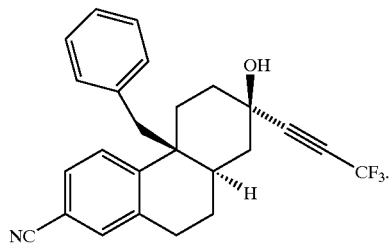

IV

The present invention relates to a compound of the formula

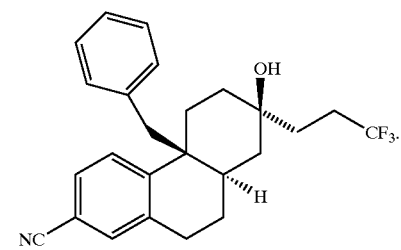

III

The present invention relates to a compound of the formula

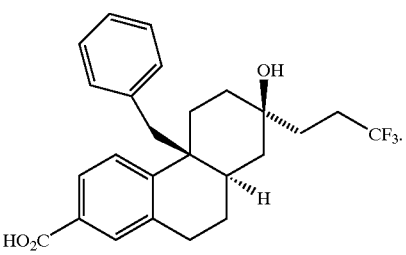

II

Detailed Description of the Invention
Preparation A

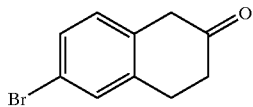

X

↓1

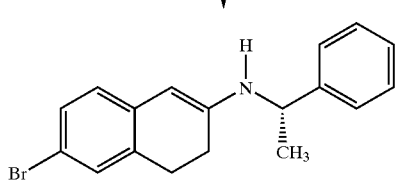

XXIII

-continued
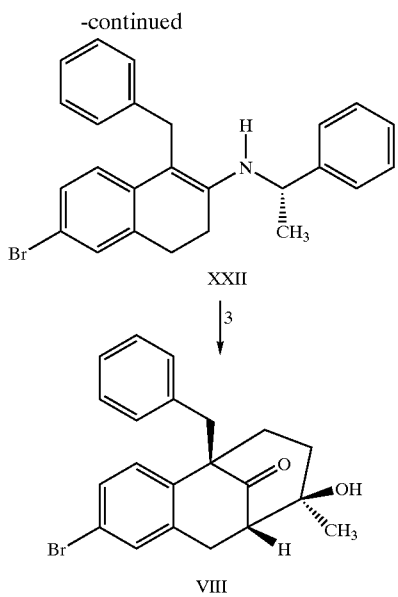
XXII
↓3
VIII
Preparation B
VII
↓1
XX
Preparation C
XIX
↓1
-continued
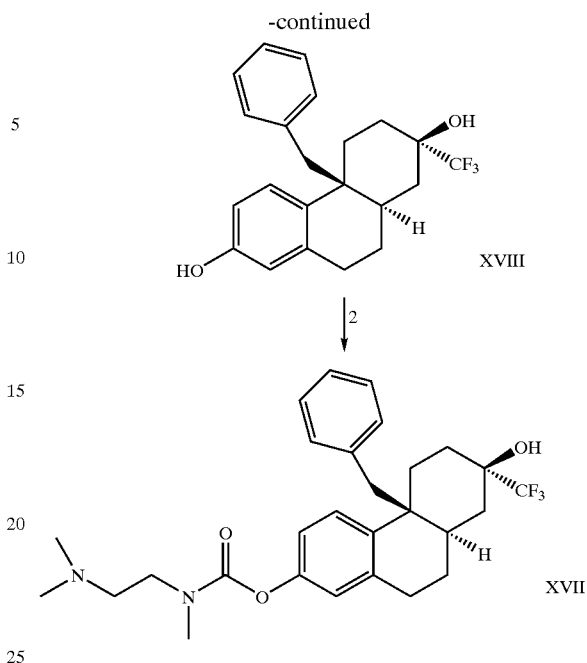
XVIII
↓2
XVII
Preparation D
XVI
↓1
XV
↓2
XIV
↓3

-continued
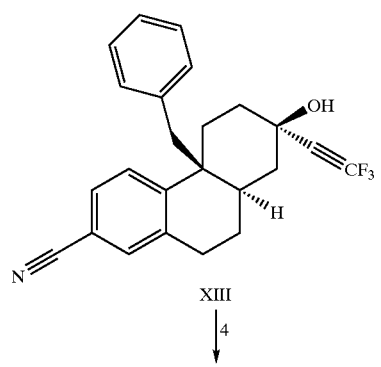
XIII
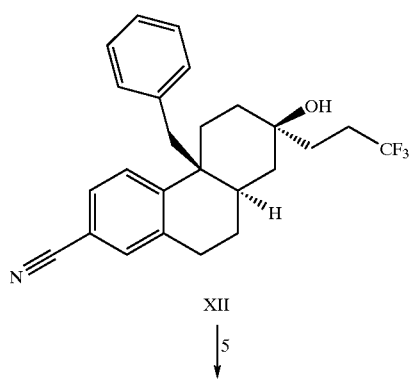
XII
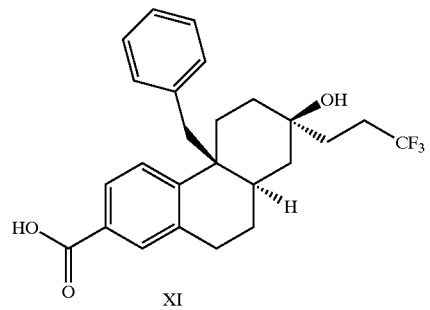
XI
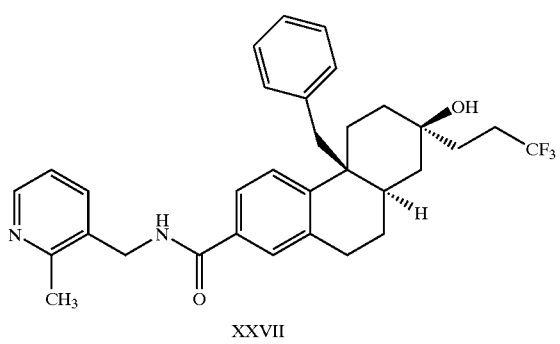
XXVII
SCHEME 1
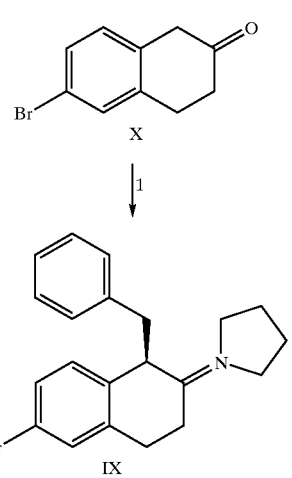
X
↓1
IX
↓2
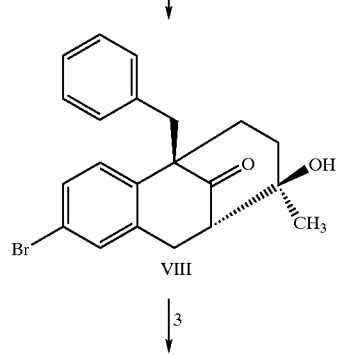
VIII
↓3
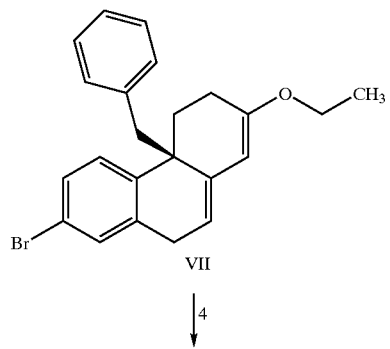
VII
↓4
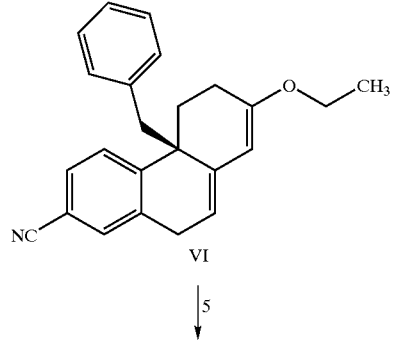
VI
↓5

-continued

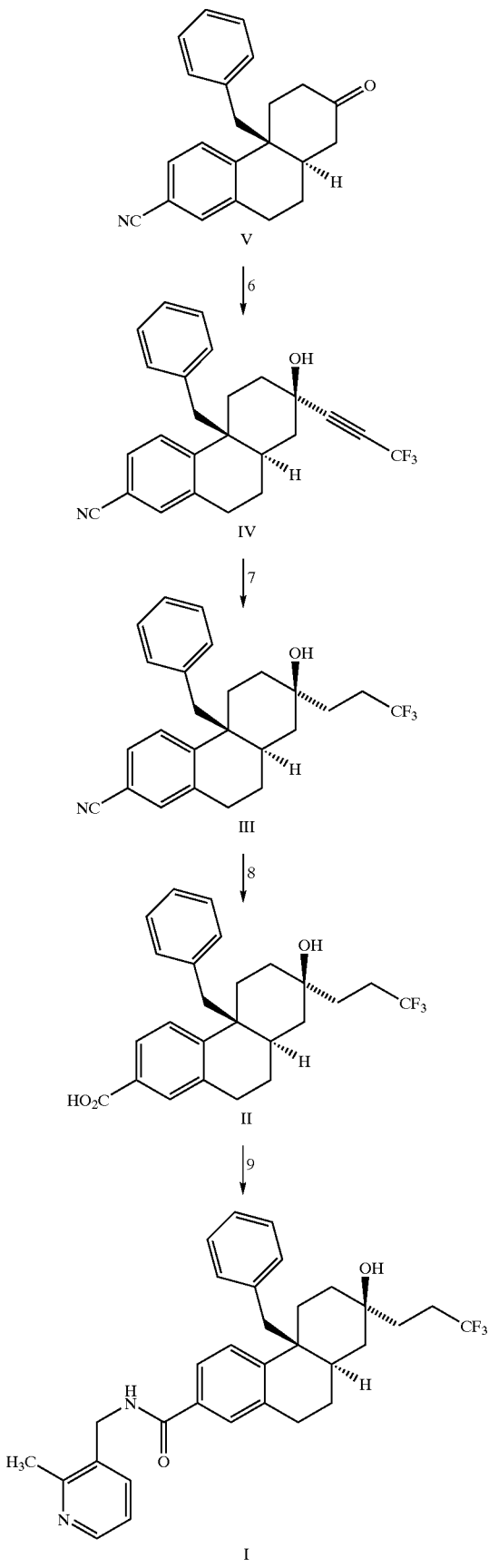

In reaction 1 of Preparation A, the compound of formula X is converted to the corresponding compound of formula XXIII, by reacting X with an amine compound of the formula

XXIV

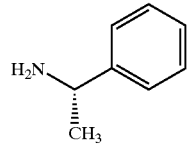

in the presence of a polar aprotic solvent, such as toluene. The reaction is stirred at a temperature between about 90° C. to about 150° C., preferably about 115° C., for a time period between about 0.5 hours to about 12 hours, preferably about 2 hours.

In reaction 2 of Preparation A, the compound of formula XXIII is converted to the corresponding compound of formula XXII, by reacting XXIII with a benzyl halide, such as benzyl bromide, in the presence of a base such as lithium diisopropylamide, and an acid, such as methanesulfonic acid. The reaction is stirred at a temperature between about −78° C. to about room temperature, preferably about 25° C., for a time period between about 0.5 hours to about 12 hours, preferably about 2 hours.

In reaction 3 of Preparation A, the compound of formula XXII is converted to the corresponding compound of formula VIII, by reacting XXII with methyl vinyl ketone in the presence of an acid, such as sulfuric acid, and a polar aprotic solvent, such as toluene. The reaction is stirred at a temperature between about −40° C. to about 180° C., preferably about 38° C., for a time period between about 0.5 hours to about 12 hours, preferably about 2 hours.

In reaction 1 of Preparation B, the compound of formula VII is converted to the corresponding compound of formula XX, by first treating VII with a base, such as n-butyl lithium, in the presence of a polar solvent, such as tetrahydrofuran. The reaction is stirred a temperature between about −100° C. to about −70° C., preferably about −78° C., for a time period between about 0.5 hours to about 12 hours, preferably about 2 hours. A borane, such as diphenylborane, or a borate, is then added to the reaction mixture and sodium hydroxide is then added in the presence of hydrogen peroxide. The resulting reaction mixture is stirred at a temperature between about −20° C. to about 0° C., preferably about −10° C., for a time period between about 0.5 hours to about 12 hours, preferably about 2 hours.

In reaction 1 of Preparation C, the compound of formula XIX is converted to the corresponding compound of formula XVIII, by reacting XIX with trimethylsilyl triflouromethane in the presence of tetrabutylammonium fluoride and a polar aprotic solvent, such as tetrahydrofuran. The reaction is stirred at a temperature between about −78° C. to about room temperature, preferably about −10° C., for a time period between about 0.5 hours to about 12 hours, preferably about 2 hours.

In reaction 2 of Preparation C, the compound of XVIII is converted to the corresponding compound of formula XVII, by reacting XVIII with a compound of the formula

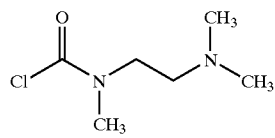

in the presence of a base. The reaction is stirred at a temperature between about −10° C. to about room temperature, preferably about 25° C., for a time period between about 0.5 hours to about 12 hours, preferably about 2 hours.

In reaction 1 of Preparation D, the compound of formula XVI is converted to the corresponding compound of formula XV, by reacting XVI with a cyanide source, such as zinc cyanide, in the presence of palladium coupling reagent, such as tetrakis(triphenylphosphine)palladium(0), and a polar protic solvent, such as dimethylformamide. The reaction is stirred at a temperature between about 25° C. to about 150° C., preferably about 80° C., for a time period between about 0.5 hours to about 12 hours, preferably about 4 hours.

In reaction 2 of Preparation D, the compound of formula XV is converted to the corresponding compound of formula XIV, by reducing XV with hydrogen, under a pressure between about 20 psi to about 100 psi, preferably about 60 psi, in the presence of a catalyst, such as palladium on carbon, and a polar solvent, such as tetrahydrofuran, followed by treating the reaction mixture with an acid, such as hydrochloric acid. The reaction is stirred at a temperature between about 0° C. to about 100° C., preferably about 25° C., for a time period between about 0.5 hours to about 12 hours, preferably about 6 hours.

In reaction 3 of Preparation D, the compound of formula XIV is converted to the corresponding compound of formula XIII, by reacting XIV with trifluoromethylpropyne in the presence of a base, such as potassium tert-butyloxy, and a polar solvent, such as tetrahydrofuran. The reaction is stirred at about −78° C. to about −25° C., preferably about −10° C., for a time period between about 0.5 hours to about 12 hours, preferably about 1 hour.

In reaction 4 of Preparation D, the compound of formula XIII is converted to the corresponding compound of formula XII, by reducing XIII with hydrogen, under a pressure between about 10 psi to about 50 psi, preferably about 20 psi, in the presence of a catalyst, such as palladium on carbon. The reaction is stirred at a temperature between about 0° C. to about 100° C., preferably about 25° C., for a time period between about 0.5 hours to about 12 hours, preferably about 6 hours.

In reaction 5 of Preparation D, the compound of formula XII is converted to the corresponding compound of formula XI, by reacting XII with 50% aqueous sodium hydroxide in ethanol. The reaction is stirred at a temperature between about 60° C. to about 100° C., preferably about 80° C., for a time period between about 0.5 hours to about 12 hours, preferably about 6 hours.

In reaction 6 of Preparation D, the compound formula XI is converted to the corresponding compound of formula XXVII, by reacting XI with an amine of the formula

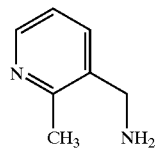

in the presence of 1,1'-carbonyldiimidazole and a polar aprotic solvent, such as tetrahydrofuran. The reaction is heated to reflux for time period between about 1 hour to about 3 hours, preferably about 2 hours.

In reaction 1 of Scheme 1, the compound of formula X is converted to the corresponding compound of formula IX by reacting X with pyrrolidine in the presence of an aprotic solvent, such as toluene. The reaction is heated to a temperature between about 80° C. to about 150° C., preferably about 115° C., for a time period between about 1 hour to about 3 hours, preferably about 2 hours. The resultant pyrrolidine enamine intermediate is then reacted with benzyl bromide, in an aprotic solvent, such as toluene, at a temperature between about 80° C. to about 100° C., preferably about 90° C., for a time period between about 30 minutes to about 3 hours, preferably about 2 hours.

In reaction 2 of Scheme 1, the compound of formula IX is converted to the compound of formula VIII by first heating IX in water and an aprotic solvent, such as toluene, at a temperature between about 25° C. to about 110° C., preferably about 100° C., for a time period between about 1 hour to about 3 hours, preferably about 2 hours. S-(−)-α-methyl benzylamine is then added to the reaction mixture and the solution was heated to a temperature between about 80° C. to about 150° C., preferably about 115° C. The intermediate so formed is then reacted with methyl vinyl ketone. The reaction mixture is then stirred at temperature between about 0° C. to about −20° C., preferably about −10° C., for a time period between about 10 minutes to about 30 minutes, preferably about 20 minutes.

In reaction 3 of Scheme 1, the compound of formula VIII is converted to the corresponding compound of formula VII by first treating VIII with sodium methoxide in the presence of a polar protic solvent, such as ethanol. The reaction mixture is stirred at a temperature between about room temperature to about 80° C., for a time period between about 1 hour to about 3 hours, preferably about 2 hours. The reaction mixture is then added to an acetylchloride ethanol solution and the resulting mixture is allowed to stir at a temperature between about −10° C. to about 10° C., preferably about 0° C., for a time period between about 15 minutes to about 1 hour, preferably about 30 minutes.

In reaction 4 of Scheme 1, the compound of formula VII is converted to the corresponding compound of formula VI by reacting VII with a cyanide source, such as zinc cyanide, in the presence of a catalyst, such as tetrakis (triphenylphosphine)palladium(0), and a polar solvent, such as dimethylformamide or dimethylacetamide. The reaction is stirred at a temperature between about 70° C. to about 90° C., preferably about 80° C., for a time period between about 10 hours to about 14 hours, preferably about 12 hours.

In reaction 5 of Scheme 1, the compound of formula VI is converted to the corresponding compound of formula V by reducing VI with hydrogen in the presence of a catalyst, such as palladium on carbon, potassium carbonate and a polar aprotic solvent, such as tetrahydrofuran. The reaction is stirred under pressure between about 40 psi to about 100 psi, preferably about 60 psi, at room temperature, for a time period about 4 hours to about 6 hours, preferably about 5 hours.

In reaction 6 of Scheme 1, the compound of formula V is converted to the corresponding compound of formula IV by reacting V with trifluoromethylpropyne in the presence of potassium tert-butoxide and a polar aprotic solvent, such as tetrahydrofuran. The reaction is stirred at a temperature between about −20° C. to about 0° C., preferably about −10° C.

In reaction 7 of Scheme 1, the compound of formula IV is converted to the corresponding compound of formula III by reducing IV with hydrogen in the presence of a catalyst, such as palladium on carbon and a polar aprotic solvent, such as tetrahydrofuran. The reaction is stirred under pressure between about 10 PSI to about 30 PSI, preferably about 20 PSI, at room temperature, for a time period between about 2 hours to about 7 hours, preferably about 5.5 hours.

In reaction 8 of Scheme 1, the compound of formula III is converted to the corresponding compound of formula II by reacting III with aqueous sodium hydroxide in the presence of a polar protic solvent, such as ethanol. The reaction is stirred at a temperature between about 70° C. to about 90° C., preferably about 80° C., for a time period between about 12 hours to about 18 hours, preferably about 15 hours.

In reaction 9 of Scheme 1, the compound of formula II is converted to the corresponding compound of formula I by reacting II with an amine of the formula

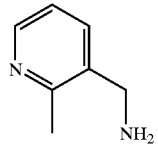

in the presence of 1,1'-carbonyldiimidazole and a polar aprotic solvent, such as tetrahydrofuran. The reaction is heated to reflux for time period between about 1 hour to about 3 hours, preferably about 2 hours.

Experimental Section

All reagents were available from commercial sources and used without purification unless stated otherwise. Melting points were determined on a Thomas Hoover capillary melting point apparatus and were uncorrected. NMR spectra were obtained on an UNITYplus-400 (400 MHz) spectrometer in deuterochloroform, acetone-$d_6$ or DMSO-$d_6$. Infrared spectra were recorded on a Nicolet Avatar 360 FT-IR. Optical rotations were determined on a Perkin-Elmer 241 polarimeter. Mass spectra were obtained at M-Scan Inc., West Chester, Pa. Elemental analyses were performed by Schwarzkopf Microanalytical Laboratory, Woodside, N.Y.

EXAMPLE 1

1-(1 (RS)-Benzyl-6-bromo-3,4-dihydro-1H-naphthalen-2-ylidene)-pyrrolidinium Bromide A solution of the bisulfite adduct of bromotetralone (250 grams, 760 mmol) in saturated sodium bicarbonate (1.25 L) and ethyl acetate (2.5 L) was stirred vigorously overnight. Phases were separated and the organic was transferred to a new flask and toluene (1 L) was added. The solution was distilled under reduced pressure to a volume of approximately 500 mL. An additional 500 mL of toluene was added and distilled under reduced pressure to a volume of approximately 300 mL. The solution was cooled to room temperature and pyrrolidine (54.1 grams, 760 mmol) was added. The reaction was heated to 150° C. under Dean-Stark conditions. After 2 hours approximately 13 mL of water was collected and concentration of a small sample showed the reaction was complete by NMR. The toluene solution of pyrrolidine enamine was cooled to 90° C. and benzyl bromide (105 mL, 912 mmol) was added dropwise. After 30 minutes solids began to granulate and the solution became very thick. An additional 500 mL of toluene was added to aid stirring and heating was continued at 90° C. for 2 hours. The slurry was allowed to cool to room temperature and granulate overnight. The solids were filtered and washed with toluene (2 times 500 mL). After drying in a vacuum oven overnight (50° C.) a brown solid was collected: 250 grams (557 mmol), 73% yield; mp 203–205° C.; IR (film) ν 1654, 1596 cm$^{-1}$; $^1$H NMR (CDCl$_3$) δ 7.25 (s, 1H), 7.17–7.13 (m, 3H), 7.08 (dd, 1H, J=8.3, 1.7 Hz), 6.98–6.93 (m, 2H), 6.68 (d, 1H, J=8.3 Hz), 4.29 (dd, 1H, J=7.5, 7.5 Hz), 4.25–4.17 (m, 2H), 3.95–3.86 (m, 1H), 3.62–3.49 (m, 2H), 3.27 (dd, 1H, J=13.7, 6.6 Hz), 3.14–3.05 (m, 3H), 2.07–1.95 (m, 3H), 1.92–1.84 (m, 1H); $^{13}$C NMR (CDCl$_3$) δ 189.2, 137.2, 136.1, 132.2, 131.2, 130.9, 130.6, 129.8, 129.2, 127.8, 122.1, 55.1, 55.2, 51.3, 39.3, 34.0, 25.6, 24.9, 24.2. Anal. calcd for C$_{21}$H$_{22}$BrN: C, 56.15; H, 5.16; N, 3.12. Found: C, 55.64; H, 5.22; N, 3.22.

EXAMPLE 2

1(R)-Benzyl-5-bromo-9(S)-hydro-10(R)-hydroxy-10(R)-methyl-tricyclo[7.3.1.0$^{2,7}$]trideca-2,4,6-trien-13-one A solution of 1-(1(RS)-Benzyl-6-bromo-3,4-dihydro-1H-naphthalen-2-ylidene)-pyrrolidinium bromide (245 grams, 545 mmol) in toluene (275 mL) and water (275 mL) was heated to 100° C. for 2 hours and then cooled to room temperature. Phases were separated and the aqueous washed with toluene (250 mL). The combined organics and (S)-(−)-α-methylbenzylamine (71 mL, 545 mmol) were heated to 150° C. under Dean-Stark conditions. Once 250 mL of toluene and water were collected the reaction was allowed to cool to room temperature and stir overnight. The solution was then cooled to −10° C. and methyl vinyl ketone (50 mL, 600 mmol), freshly distilled from potassium carbonate under reduced pressure, was added dropwise over 15 minutes. Once addition was complete the reaction was stirred at −10° C. for 20 minutes and then allowed to warm to room temperature. The solution was heated to 38° C. and monitored by NMR. After 7 hours, no starting material was observed and the reaction was cooled to room temperature. 10% sulfuric acid (750 mL) was added and the solution was stirred overnight during which time solids precipitated out of solution. These solids were filtered and washed with water (500 mL) and isopropyl ether (1000 mL). After drying in a vacuum oven (45° C.) overnight a light brown solid was collected: 159 grams (413 mmol), 76% yield; mp154–155° C.; IR (film) ν 3412, 1717 cm$^{-1}$; [α]$^{25}_D$ −48.75; $^1$H NMR (CDCl$_3$) δ 7.26–7.19 (m, 2H), 7.13–7.08 (m, 2H), 7.06–7.00 (m, 4H), 3.72 (d, 1H, J=15.8Hz), 3.35 (dd, 1H, J=18.0, 6.6 Hz), 3.12 (d, 2H, j=15.8 Hz), 3.11 (d, 1H, J=18.0 Hz), 2.66 (d, 1H, J=6.6 Hz), 2.28 (ddd, 1H, J=13.1, 13.1, 4.5 Hz), 2.06 (bs, 1H), 1.67 (ddd, 1H, J=13.1, 4.5, 2.7 Hz), 1.57–1.50 (m, 1H), 1.44–1.38 (m, 1H), 1.36 (s, 3H); $^{13}$C NMR (CDCl$_3$) δ 212.9, 139.6, 138.4, 136.8, 130.5, 130.4, 130.4, 128.7, 128.1, 125.8, 120.6, 79.3, 58.4, 54.2, 41.9, 38.5, 34.0, 32.9, 28.1. Anal. Calcd for C$_{21}$H$_{21}$BrO$_2$: C, 65.46; H, 5.49. Found: C, 65.42; H, 5.44. The structure and absolute configuration were confirmed by single crystal X-ray analysis.

EXAMPLE 3

4a(S)-Benzyl-7-bromo-2-ethoxy-3,4,4a,9-tetrahydro-phenanthrene

Sodium methoxide (8.4 grams, 156 mmol) was added slowly to a solution of 1-(1(RS)-Benzyl-6-bromo-3,4-dihydro-1H-naphthalen-2-ylidene)-pyrrolidinium bromide (60 grams, 156 mmol) in 2B ethanol (540 mL) and stirred for 4 hours at 80° C. HPLC showed starting material was consumed and the reaction was cooled to −10° C. Acetyl-chloride (33 mL, 467 mmol) as a solution in 2B ethanol (180 mL) was also cooled to −10° C. The reaction mixture was added slowly to the acetyl chloride solution such that the temperature remained at approximately 0° C. Once addition was complete the resulting solids were allowed to granulate for 1 h at 0° C. The solids were filtered and washed with 2B ethanol (2 times 100 mL) and placed in a vacuum oven at room temperature overnight. The resulting solids contained 7.59% sodium chloride ash and could be taken on without purification. After drying in a vacuum oven overnight (room temperature) a pale yellow solid was collected: 56.1 grams (131 mmol), 84% yield; mp 134–135° C.; IR (film) ν 1656, 1631 cm$^{-1}$; [α]$^{25}_D$+170.68; $^1$H NMR (acetone-d$_6$) δ 7.37–7.32 (m, 2H), 7.11–7.05 (m, 2H), 7.01–6.95 (m, 2H), 6.53 (d, 2H, J=7.1 Hz), 5.49 (dd, 1H, J=5.8, 2.5 Hz), 5.47 (d, 1H, J=1.2 Hz), 3.91 ( q, 2H, J=7.1 Hz), 3.03 (d, 1H, J=12.5 Hz), 2.91 (dd, 1H, J=21.6, 5.8 Hz), 2.77–2.69 (m, 1H), 2.68 (d, 1H, J=12.5 Hz), 2.59 (dd, 1H, J=12.9, 6.0 Hz), 2.27 (dd, 1H, J=17.1, 6.0 Hz), 2.13 (d, 1H, J=21.6 Hz), 1.79 (ddd, 1H, J=12.9, 12.9, 5.8 Hz), 1.32 (t, 3H, J=7.1 Hz); $^{13}$C NMR (acetone-d$_6$) δ 155.2, 141.1, 140.1, 137.8, 136.2, 130.7, 129.9, 128.8, 127.9, 127.1, 126.0, 119.3, 118.7, 98.9, 62.5, 44.3, 41.9, 32.4, 30.0, 25.6, 14.3. Anal. Calcd for C$_{23}$H$_{23}$BrO: C, 69.88; H, 5.86. Found: C, 70.20; H, 5.84.

EXAMPLE 4

4b(S)-Benzyl-7-ethoxy-4b,5,6,10-tetrahydro-phenanthrene-2-carbonitrile

Zinc cyanide (13.4 g, 114 mmol) was added to a solution of 4a(S)-Benzyl-7-bromo-2-ethoxy-3,4,4a,9-tetrahydro-phenanthrene (30 grams, 75.9 mmol) in DMF (200 mL) followed by tetrakis(triphenylphosphine)palladium(0), (10.5 g, 9.11 mmol) in a flask outfitted with a bleach scrubbing system. Additional dimethyl formamide (400 mL) was used to wash the sides of the flask and funnel. The suspension was heated to 80° C. After 7 hours HPLC showed no starting material and the reaction was cooled to room temperature. The suspension was diluted with EtOAc (300 mL) and filtered through a pad of Celite. The filtrate was washed with 2N NH$_4$OH (2 times 500 mL), brine (500 mL) and water (500 mL). Upon addition of water solids began to precipitate out so additional EtOAc (200 mL) was added. The organic layer was concentrated to ½ volume and diluted with ethanol (250 mL) and water (250 mL). The resulting solids were allowed to granulate for 1 hour and then filtered. The mother liquor was concentrated slightly and a second crop was collected. After the combined crops air dried overnight a white solid was collected: 24.9 grams (72.9 mmol), 96% yield; mp 164–165° C., IR (film) ν 2227, 1657, 1631 cm$^{-1}$; [α]$^{25}_D$+160.06; $^1$H NMR (acetone-d$_6$) δ 7.62–7.56 (m, 2H), 7.29 (s, 1H), 7.09–7.06 (m, 1H), 7.01–6.95 (m, 2H), 6.51 (d, 2H, J=7.1 Hz), 5.54 (dd, 1H, J=5.4, 2.0 Hz), 5.49 (d, 1, J=1.6 Hz), 3.91 (q, 2, J=7.1 Hz), 3.07 (d, 1, J=12.5 Hz), 2.99 (dd, 1, J=21.6, 5.8 Hz), 2.81–2.72 (m, 1H), 2.73 (d, 1H, J=12.5 Hz), 2.65 (dd, 1H, J=13.7, 6.6 Hz), 2.29 (dd, 1H, J=17.8, 5.4 Hz), 2.15 (d, 1H, J=21.6 Hz), 1.83 (ddd, 1H, J=12.8, 12.8, 6.2 Hz), 1.33 (t, 3H, J=7.1 Hz); $^{13}$C NMR (acetone-d$_6$) δ 155.3, 147.4, 138.9, 137.4, 136.0, 131.0, 130.7, 129.5, 127.2, 127.0, 126.2, 119.0, 118.4, 109.5, 98.8, 62.5, 44.2, 42.5, 32.1, 29.9, 25.5, 14.3. Anal. Calcd for C$_{24}$H$_{23}$NO: C, 84.42; H, 6.79; N, 4.10. Found: C, 83.82; H, 6.87; N, 4.04. The structure and absolute configuration were confirmed by single crystal X-ray analysis.

EXAMPLE 5

4b(S)-Benzyl-7-oxo-4b,5,6,7,8,8a(R),9,10-octahydro-phenanthrene-2-carbonitrile.

To a solution of water wet 5% palladium on carbon (7.0 grams) and K$_2$CO$_3$ (7.0 g) in THF (100 mL) was added 4b(S)-Benzyl-7-ethoxy4b,5,6,10-tetrahydro-phenanthrene-2-carbonitrile (35.0 g, 103 mmol) in tetrahydrofuran (600 mL). The resulting slurry was transferred to a 1L hydrogenator with overhead stirring under 50 psi of hydrogen. After 5 hours no starting material could be detected by HPLC and the reaction mixture was filtered through a pad of Celite. The filtrate was diluted with 1N hydrochloric acid (70 mL) and after standing for 1 hour no vinyl ether could be detected by HPLC. The solution was diluted with EtOAc (700 mL), water (700 mL) and brine (100 mL) and phases were separated. The organic was washed with water (700 mL) and brine (700 mL). The organic was concentrated under reduced pressure to approximately 500 mL and EtOAc (500 mL) was added and the solution concentrated again to approximately 300 mL. To the vigorously stirring solution were added hexanes (1 L) in one portion. The resulting solids were allowed to granulate for 1 hour and then filtered. HPLC showed some impurities so the solids were allowed to granulate in hexanes (75 mL) and EtOAc (25 mL) for 24 hours. The solids were filtered and allowed to air dry. The mother liquor was concentrated to give orange solids, which were granulated in EtOAc (15 mL) and hexanes (85 mL) for 24 hours. The solids were filtered and combined with the first crop. After air drying overnight a white solid was collected: 18 grams (57.1 mmol), 56% yield; mp 128–129 ° C.; IR (film) ν 2226, 1713 cm$^{-1}$; [α]$^{25}_D$–252.50; $^1$H NMR (CDCl$_3$) δ 7.43 (s, 1H), 7.21–7.08 (m, 4H), 6.58 (d, 2H, J=7.1 Hz), 6.40 (d, 1H, J=7.9 Hz), 3.21 (d, 1H, J=13.3 Hz), 3.13–2.97 (m, 2H), 2.85 (ddd, 1H, J=14.9, 14.9, 6.2 Hz), 2.80 (d, 1H, J=14.1 Hz), 2.66–2.51 (m,2H), 2.60 (d, 1H, J=14.1 Hz), 2.45–2.40 (m, 1H), 2.24–2.1 (m, 1H), 2.09–1.98 (m, 1H), 1.83–1.76 (m, 1H), 1.61 (dd, 1H, J=14.1, 14.1, 5.4 Hz); $^{13}$C NMR (CDCl$_3$) δ 210.1, 147.6, 137.3, 136.5, 133.1, 130.9, 128.4, 128.1, 128.0, 127.0, 119.3, 110.4, 44.5, 42.7, 40.7, 38.2, 36.2, 33.0, 28.0, 24.7. Anal. Calcd for C$_{22}$H$_{2}$NO: C, 83.77; H, 6.71; N, 4.44. Found: C, 83.76; H, 6.90; N, 4.40. The structure and absolute configuration were confirmed by single crystal X-ray analysis.

EXAMPLE 6

4b(S)-Benzyl-7(R)-hydroxy-7(R)-trifluoroprop-1-ynyl-4b,5,6,7,8,8a(R),9,10-octahydro-phenanthrene-2-carbonitrile To a solution of 4b(S)-Benzyl-7-oxo-4b,5,6,7,8,8a(R),9,10-octahydro-phenanthrene-2-carbonitrile. (20 grams, 63.4 mmol) in tetrahydrofuran (320 mL) cooled to –10° C. was added 3,3,3-triflouro-1-propyne (42 mL as a ~3 M solution in tetrahydrofuran, 127 mmol). Potassium t-butoxide (12.7 mL as a 1.0 M solution in tetrahydrofuran, 12.7 mmol) was added via addition funnel to the solution to keep temperature at approximately –10° C. (approximately 7 minutes). Once addition was complete HPLC showed starting material was consumed and the product was observed as a 10:1 ratio of diastereomers. The reaction was quenched with water (1.14 mL, 63.4 mmol) and warmed to room temperature. The resulting solution can be taken on crude. Isolation begins by washing the organic with sat NH$_4$Cl (200 mL) and brine (2 times 200 mL). The organic layer was dried (Na$_2$SO$_4$), decanted and concentrated. After drying under high vacuum overnight a light brown foamy solid was collected: mp 73–75° C.; IR (film) ν 3409, 2275, 2230 cm$^{-1}$; [α]$^{25}_D$–196.02; $^1$H NMR (major diastereomer) (CDCl$_3$) δ 7.44 (s, 1H), 7.18–7.07 (m, 4H), 6.51 (d, 2H, J=7.1 Hz), 6.41 (d, 1H, J=8.3 Hz), 3.09–3.00 (m, 3H), 2.60 (d, 1H, J=13.3 Hz), 2.27–2.20 (m, 3H), 2.08–1.93 (m, 4H), 1.90–1.80 (m, 1H), 1.47–1.41 (m, 1H); $^{13}$C NMR (major diastereomer) (CDCl$_3$) δ 148.8, 137.5, 136.8, 133.1, 131.0, 128.1, 127.9, 127.8, 126.7, 119.4, 114.3 (q, J=257.1 Hz), 110.0, 90.4 (q, J=6.1 Hz), 72.1 (q, J=54.1 Hz), 69.1, 41.4, 40.5, 39.5, 35.9, 35.4, 30.0, 27.3, 23.8. HRMS (EI) calcd for protonated C$_{25}$H$_{22}$F$_3$NO m/e 410.1732, found m/e 410.1758.

Alternate synthesis: To a solution of 2 (1.0 g, 3.17 mmol) and 16 (726 mg, 3.49 mmol) in THF (20 mL) cooled to −15° C. TBAF (3.49 mL as a 1.0 M solution in THF, 3.49 mmol) was slowly to keep temperature below −10° C. Once addition was complete HPLC showed a 7:1 ratio of diastereomers favoring the axial propyne stereochemistry. The reaction was quenched with water (63 mg, 3.49 mmol) and warmed to room temperature. The resulting reaction mixture could them be used without further isolation or purification. All characteristics were identical to those of compound isolated from the above method.

EXAMPLE 7

4b(S)-Benzyl-7(S)-hydroxy-7(S)-(3,3,3-trifluoro-propyl)-4b,5,6,7,8,8a(R),9,10-octahydro-phenanthrene-2-carbonitrile To a tetrahydrofuran (245 mL) solution of 4b(S)-Benzyl-7(R)-hydroxy-7(R)-trifluoroprop-1-ynyl-4b,5,6,7,8,8a(R),9,10-octahydro-phenanthrene-2-carbonitrile (17.3 grams, 42.3 mmol) in a Parr bottle was added wet 5% palladium on carbon (2.0 grams) slurried in tetrahydrofuran (5 mL). The reaction was placed on a Parr shaker under 20 psi of hydrogen. After 2.5 hours, hydrogen uptake slowed and ceased after an additional 3 hours. The reaction mixture was filtered through a pad of Celite and the filtrate concentrated. After drying under high vacuum overnight a light brown foamy solid was collected: mp 70–72° C.; IR (film) ν 3454, 2228 cm$^{-1}$; $[\alpha]^{25}{}_D$−180.73; $^1$H NMR (CDCl$_3$)(major diastereomer) δ 7.42 (s, 1H), 7.17–7.07 (m, 4H), 6.51 (d, 2H, J=6.7 Hz), 6.39 (d, 1H, J=8.3 Hz), 3.13 (d, 1H, J=13.2 Hz), 3.12–2.96 (m, 2H), 2.57 (d, 1H, J=13.2 Hz), 2.26–2.10 (m, 3H), 2.06 (ddd, 1H, J=14.1, 14.1, 3.8 Hz), 2.03–1.67 (m, 8H), 1.23 (ddd, 1H, J=14.1, 14.1, 3.3 Hz); $^{13}$C NMR (CDCl$_3$) (major diastereomer) δ 149.4, 137.5, 137.0, 133.0, 131.0, 128.1, 128.0, 127.9, 127.8 (q, J=275.2 Hz), 126.6, 119.5, 110.0, 71.4, 41.2, 40.9, 39.3, 35.6, 34.5, 29.9, 29.6, 28.3 (q, J=28.6 Hz), 27.3, 24.2. HRMS (EI) calcd for prtonated C$_{25}$H$_{26}$F$_3$NO m/e 414.2045, found m/e 414.2050.

EXAMPLE 8

4b(S)-Benzyl-7(S)-hydroxy-7(S)-(3,3,3-trifluoro-propyl)-4b,5,6,7,8,8a(R),9,10-octahydro-phenanthrene-2-carboxylic acid A solution of 4b(S)-Benzyl-7(S)-hydroxy-7(S)-(3,3,3-trifluoro-propyl)-4b,5,6,7,8,8a(R), 9,10-octahydro-phenanthrene-2-carbonitrile (10 grams, 24.2 mmol) in 2B ethanol (200 mL) and 50% sodium hydride (25 mL) was heated to 80° C. After 15 hours no starting material or intermediate amide could be detected by HPLC. The solution was cooled to 0° C. and concentrated hydrochloric acid was added dropwise until reaching pH of 6.3. The resulting solution was washed with EtOAc (2 times 250 mL) and the combined organics were concentrated to approximately 50 mL. Hexanes (200 mL) were added slowly via addition funnel generating solids, which were allowed to granulate. The solids were filtered and the mother liquor resubmitted to crystallization conditions generating a second crop, which was added to the first. After air drying overnight a white solid containing no observable diastereomer by HPLC was collected: 6.5 grams (15.1 mmol), 63% yield for 3 steps; mp 128–130° C.; IR (film) ν 2938, 1689 cm$^{-1}$; $[\alpha]^{25}{}_D$−143.10; $^1$H NMR (DMSO-d$_6$) δ 12.74 (bs, 1H), 7.67 (s, 1H), 7.34 (dd, 1H, J=8.3, 1.6 Hz), 7.10–7.03 (m, 3H), 6.49 (d, 2H, J=7.9 Hz), 6.34 (d, 1H, J=8.3 Hz), 4.65 (bs, 1H), 3.07 (d, 1H, J=13.2 Hz), 3.06–2.90 (m, 2H), 2.56 (d, 1H, J=13.2 Hz), 2.30–2.17 (m, 2H), 2.04–1.95 (m, 2H), 1.86–1.77 (m, 1H), 1.70–1.59 (m, 6H), 1.54 (d, 1H, J=12.0 Hz), 1.21–1.07 (m, 1H); $^{13}$C NMR (CDCl$_3$) δ 172.2, 150.1, 137.2, 136.5, 131.3, 131.0, 131.0, 127.8, 127.8 (q, J=276.5 Hz), 127.3, 126.5, 126.3, 71.8, 41.3, 40.9, 39.5, 35.7, 34.6, 30.0, 29.6, 28.3 (q, J=29.0 Hz), 27.5, 24.5. Anal. calcd for C$_{25}$H$_{27}$F$_3$O$_3$: C, 69.43; H, 6.29; F, 13.18. Found: C, 69.77; H, 7.02; F, 12.02.

EXAMPLE 9

4b(S)-Benzyl-7(S)-hydroxy-7(S)-(3,3,3-trifluoro-propyl)-4b,5,6,7,8,8a(R),9,10-octahydro-phenanthrene-2-carboxylic acid (2-methyl-pyridin-3-ylmethyl)-amide To a solution of 4b(S-Benzyl-7(S)-hydroxy-7(S)-(3,3,3-trifluoro-propyl)-4b,5,6,7,8,8a(R),9,10-octahydro-phenanthrene-2-carboxylic acid (1.0 grams, 2.31 mmol) in tetrahydrofuran (20 mL) 1,1'-carbonyldiimidazole (450 mg, 2.77 mmol) was added. The reaction was refluxed and after 2 hours. HPLC, 1 mL/min; intermediate$_T$ 8.3 minutes) showed no starting material. After the reaction was cooled to room temperature amine (339 mg, 2.77 mmol) dissolved in tetrahydrofuran (1 mL) was added. After 3 hours at room temperature HPLC, 1 mL/min; CP-628006$_T$ 4.7 min) showed no intermediate. To the solution water (50 mL) and EtOAc (50 mL) were added and the phases separated. The organic phase was washed with saturated NH$_4$Cl (2 times 50 mL) and concentrated. The resulting light brown foam was dissolved in hot acetone and inorganic salts were filtered off. The filtrate was concentrated and the resulting material suspended in EtOAc (15 mL). The resulting slurry was heated on a steam bath until approximately 5 mL EtOAc remained. The suspension was cooled to room temperature and the solids that precipitated were granulated overnight. The solids were filtered and the mother liquor was resubjected to the same crystallization process and a second crop was collected and combined with the first. After air drying overnight a white solid which was 97% pure by HPLC, 25% CH$_3$CN, 10% MeOH, 1 mL/min; 16.2 min) was collected: 851 mg (1.59 mmol); 69% yield; mp 219–220° C.; IR (film) ν 3324, 1640 cm$^{-1}$; $[\alpha]^{25}{}_D$−130.00; $^1$H NMR (DMSO-d$_6$) δ 8.86 (dd, 1H, J=5.6, 5.6 Hz), 8.30 (dd, 1H, J=4.7, 1.5 Hz), 7.66 (dd, 1H, J=1.5 Hz), 7.54 (dd, 1H, J=7.5, 1.2 Hz), 7.34 (dd, 1H, J=8.1, 1.5 Hz), 7.15 (dd, 1H, J=7.5, 4.7 Hz), 7.11–7.05 (m, 2H), 6.53–6.50 (m, 2H), 6.34 (d, 1H, J=8.3 Hz), 4.63 (s, 1H), 4.42 (d, 2H, J=6.2 Hz), 3.06 (d, 1H, J=12.9 Hz), 2.49 (s, 3H), 2.33–2.19 (m, 2H), 2.06–1.93 (m, 2H), 1.88–1.77 (m, 1H), 1.70–1.57 (m, 6H), 1.54 (1H, J=12.0 Hz), 1.16–1.09 (m, 1H); $^{13}$C NMR (CDCl$_3$) δ 167.8, 156.7, 148.2, 147.8, 137.3, 136.8, 136.6, 132.0, 131.6, 131.1, 128.4, 127.9 (q, J=276.6 Hz), 127.8, 127.3, 126.4, 122.7, 121.9, 71.5, 41.6, 41.3, 40.6, 39.6, 35.7, 34.6, 30.1, 29.6, 28.3 (q, J=28.6 Hz), 27.6, 24.5, 22.1. Anal. Calcd for C$_{32}$H$_{35}$F$_3$N$_2$O$_2$: C, 71.62; H, 6.57; N, 5.22; F, 10.62. Found: C, 72.04; H, 6.54; N, 5.33; F, 10.65.

What is claimed is:

1. A process for preparing a compound of the formula

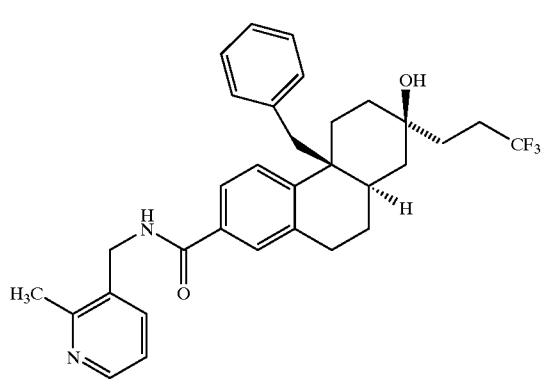

I comprising reacting a compound of the formula

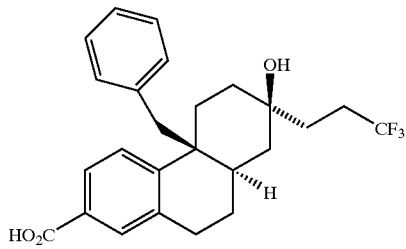
II with an amide of the formula

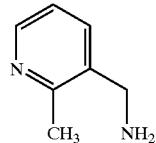

in the presence of 1,1'-carbonyldiimazole.

2. A process according to claim 1, wherein the compound of formula II is formed

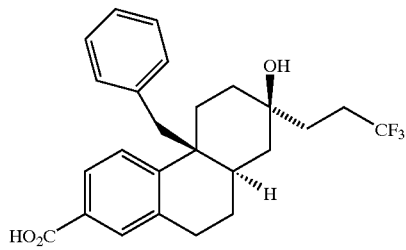
II comprising reacting a compound of the formula

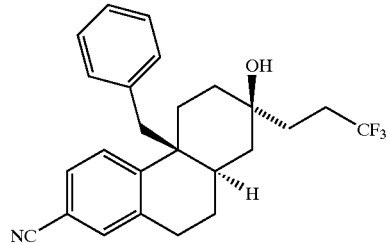
III with aqueous sodium hydroxide in a polar protic solvent.

3. A process according to claim 2, wherein the compound of formula III is formed

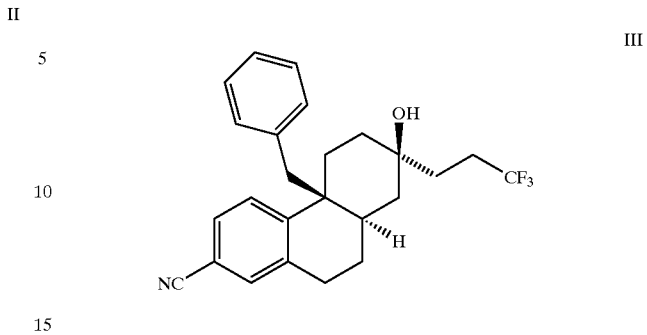
III comprising reducing a compound of the formula

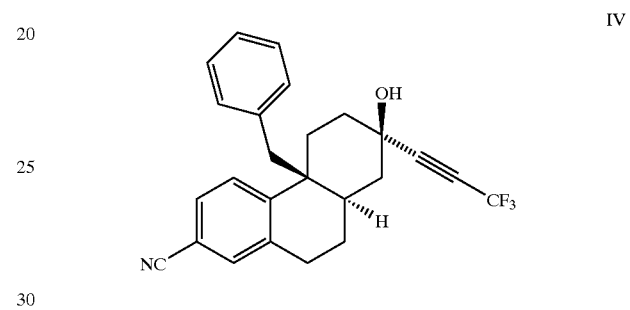
IV with hydrogen in the presence of a catalyst.

4. A process according to claim 3, wherein the compound of formula IV is formed

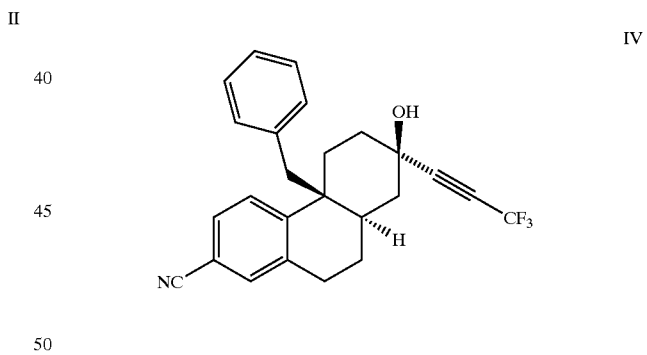
IV comprising reacting the compound of the formula

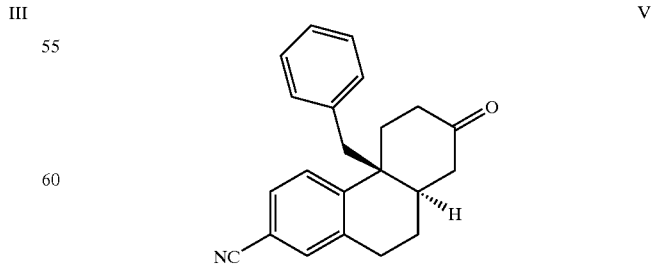
V with trifluoromethylpropyne.

5. A process according to claim 4, wherein the compound of formula V is formed

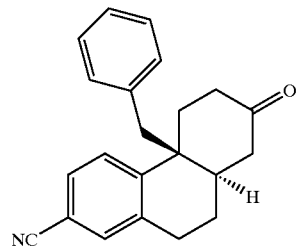

comprising reducing a compound of the formula

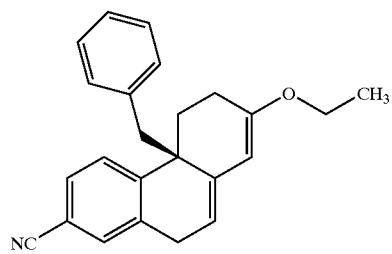

with hydrogen in the presence of a catalyst and potassium carbonate.

6. A process according to claim 5, wherein the compound of formula VI is formed

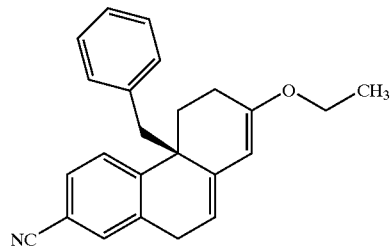

comprising reacting a compound of the formula

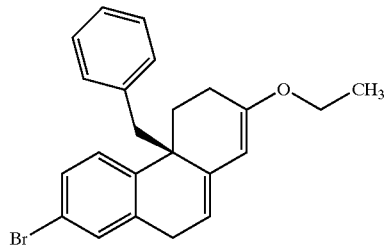

with a cyanide source in the presence of a catalyst.

7. A process according to claim 6, wherein the compound of formula VII is formed

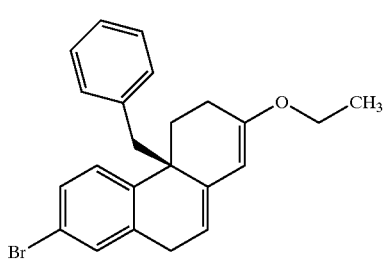

comprising reacting a compound of the formula

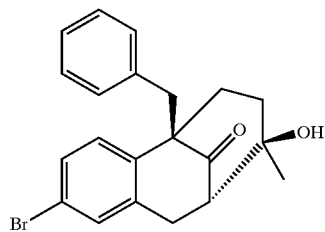

with sodium methoxy.

8. A process according to claim 7, wherein the compound of formula VIII is formed

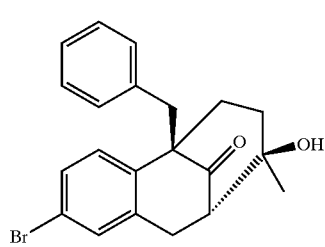

comprising reacting a compound of the formula

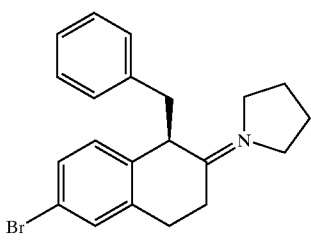

with methyl vinyl ketone.

9. A process according to claim 8, wherein the compound of formula IX is formed

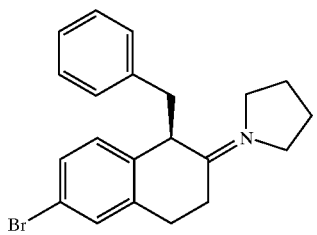

IX comprising reacting a compound of the formula

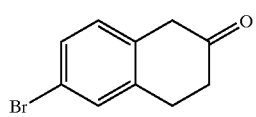

X with pyrrolidine followed by reacting the resultant pyrrolidine enamine intermediate with a benzyl halide.

10. A process for preparing a compound of the formula

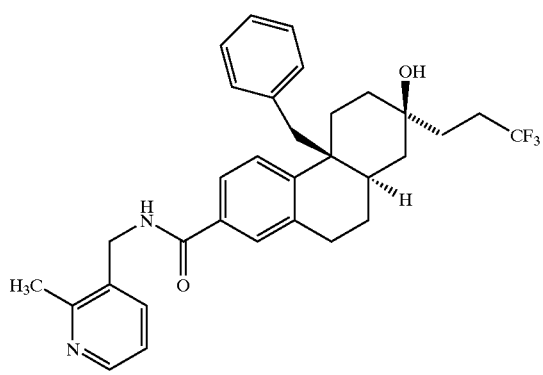

I comprising (a) reacting a compound of the formula

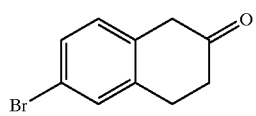

X with pyrrolidine followed by reacting the resultant pyrrolidine enamine intermediate with a benzyl halide to form the compound of formula IX

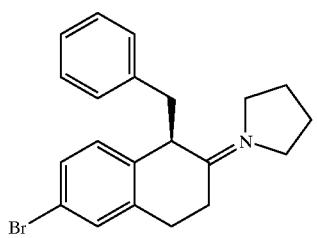

IX (b) reacting the compound of formula IX so formed with methyl vinyl ketone to form the compound of formula VIII

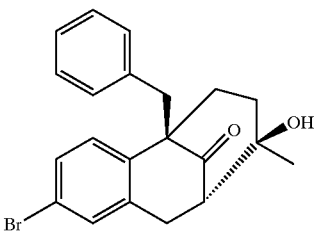

VIII (c) reacting the compound of formula VIII so formed with sodium methoxy to form the compound of formulas VII

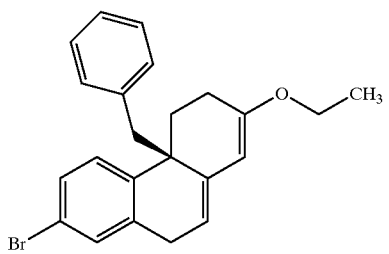

VII (d) reacting the compound of formula VII so formed with a cyanide source in the presence of a catalyst to form the compound of formula VI

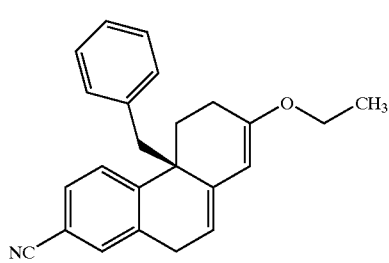

VI (e) reducing the compound of formula VI so formed with hydrogen in the presence of a catalyst and potassium chloride to form the compound of formula V

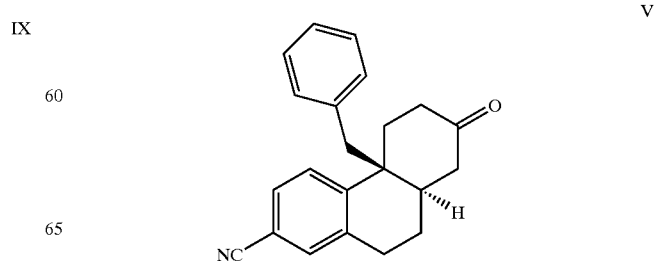

V (f) reacting the compound of formula V so formed with trifluoromethylpropyne to form the compound of formula IV

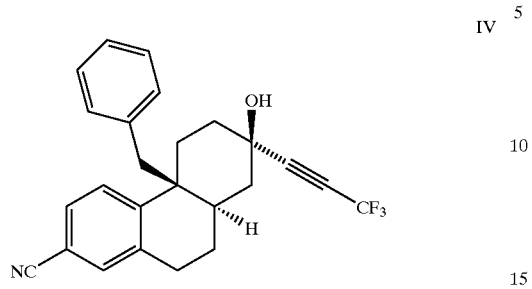

IV (g) reducing the compound of formula IV so formed with hydrogen in the presence of a catalyst to form the compound of formula III

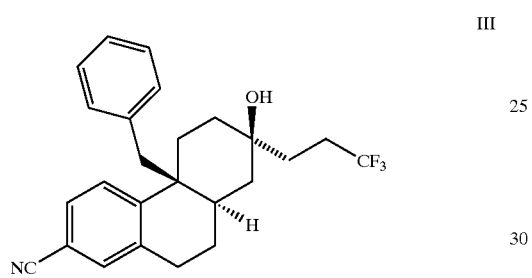

III (h) reacting the compound of formula III so formed with aqueous sodium hydroxide in a polar protic solvent to form the compound of formula II

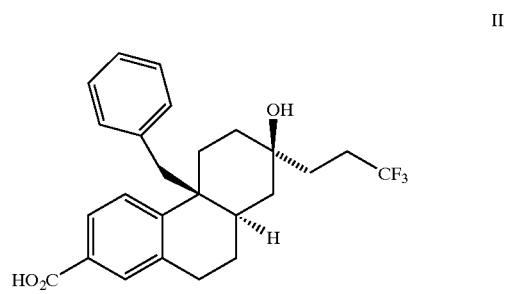

II (ii) reacting the compound of formula II so formed with an amide of the formula

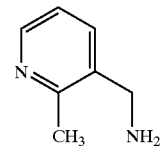

in the presence of 1,1'-carbonyldiimazole.

* * * * *